United States Patent [19]

Hein et al.

[11] 4,051,253

[45] Sept. 27, 1977

[54] MICROBICIDAL NITROFURYL COMPOUNDS

[75] Inventors: Helmut Hein; Rosmarie Hermann geb Gleissner; Hartmann Schaefer, all of Constance, Germany

[73] Assignee: Byk Gulden Lomberg Chemische Fabrik GmbH, Constance, Germany

[21] Appl. No.: 621,529

[22] Filed: Oct. 10, 1975

[30] Foreign Application Priority Data

Oct. 15, 1974 Luxembourg ............................ 71111

[51] Int. Cl.$^2$ ...................... A01N 9/28; C07D 307/34
[52] U.S. Cl. .................................. 424/285; 260/347.3; 542/408
[58] Field of Search ................... 424/285; 260/240 A, 260/347.3

[56] References Cited

U.S. PATENT DOCUMENTS

| 3,127,420 | 3/1964 | Ebetino et al. | 260/347.3 |
| 3,701,773 | 10/1972 | Minami et al. | 260/240 A |
| 3,847,911 | 11/1974 | Szarvasi et al. | 260/240 A |

OTHER PUBLICATIONS

Chemical Abstracts, 52:20388f–20389b.
Sasaki et al., Bull. Chem. Soc. of Japan, vol. 43, pp. 2989–2990, (1970).

Primary Examiner—Leonard Schenkman
Attorney, Agent, or Firm—Berman, Aisenberg & Platt

[57] ABSTRACT

2-[(o-alkylaroylhydrazono)propen-1-yl]-5-nitrofurans [1] are prepared by condensing 3-(5-nitro-2-furyl)acrylaldehyde [2] with an o-alkylaroyl hydrazide [3]. Compounds [1] are bactericides, protozoacides and fungicides and are administrable to animals in therapeutically-acceptable compositions.

18 Claims, No Drawings

MICROBICIDAL NITROFURYL COMPOUNDS

SUMMARY OF THE INVENTION

The invention is directed to microbicidal 2-[(o-alkylaroylhydrazono)propen-1-yl]-5-nitrofurans [I], their synthesis, compositions containing them and their use. The aromatic structure of the aroyl is preferably, but not necessarily, a single carbocyclic, e.g. a benzene, ring, which is optionally further substituted. In addition to the o-alkyl substituent on the aromatic ring, there is, optionally, one (and possibly two) further substituents thereon. Such substituents are such that they do not neutralize or destroy the microbicidal activity of [I].

[I] is used in the form of pharmaceutically-acceptable compositions as chemotherapeutically-active medicines for combatting provocative agents of human and animal disease processes. It is used, e.g., as a trichomonacide in the same manner as metronidazol. Compounds [I] have a very low toxicity to mammals and birds when administered thereto orally, parenterally or topically.

DETAILS

Nitrofuryl compounds of the general formula I

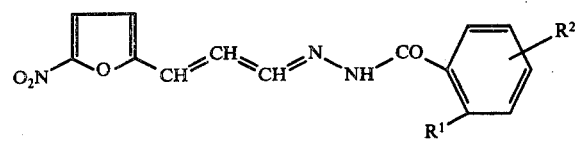

wherein $R^1$ represents an alkyl group, such as lower alkyl, e.g. alkyl containing up to 6 carbon atoms, and $R^2$ represents —H, halo (e.g. chloro or bromo), —OH, nitro, amino (—NH$_2$) or an alkyl group, such as lower alkyl, e.g. alkyl containing up to 4 carbon atoms.

Nitrofuryl compounds of the general formula I*

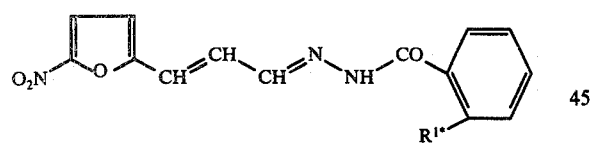

in which $R^{1*}$ represents an alkyl group containing up to 6, preferably up to 4, carbon atoms are preferred.

Excellent compounds are characterized by the formula

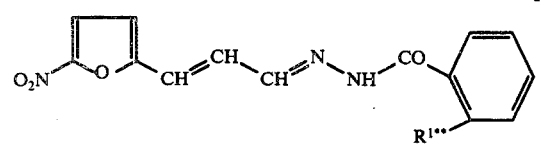

in which $R^{1**}$ represents a straight-chain alkyl group containing up to 4 carbon atoms.

The alkyl group containing up to 6, preferably up to 4, carbon atoms is a straight-chain or branched radical. Suitable straight-chain alkyl radicals include methyl, ethyl, propyl, butyl, pentyl, and hexyl. Branched alkyl radicals contain from 3 to 6 carbon atoms and include isopropyl, secondary butyl, tertiary butyl, 3-methylbutyl, 1,1- or 2,2- dimethylbutyl, 1-, 2- or 3-methylpentyl, and 1,1-, 2,2-, or 3,3-dimethylbutyl.

5-Nitro-2-[(o-toluoylhydrazono)propen-1-yl]furan and 2-[(o-ethylbenzoylhydrazono)propen-1-yl]-5-nitrofuran are primary examples.

Another aspect of the invention is a method for producing the new nitrofuryl compounds of formula I. Characteristic of the method is a reaction of 3-(5-nitro-2-furyl)acrylaldehyde

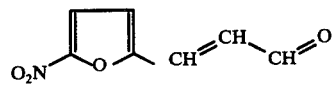

with an aromatic carboxylic acid hydrazide (aroyl hydrazide) of the formula

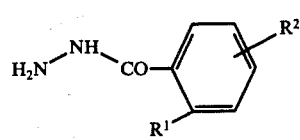

in which $R^1$ represents an alkyl group containing up to 6 carbon atoms, and $R^2$ represents —H, halo (e.g. —Cl or —Br), —OH, nitro, amino (—NH$_2$) or an alkyl group containing up to 4 carbon atoms.

In a preferred embodiment, an aromatic carboxylic acid hydrazide of the formula

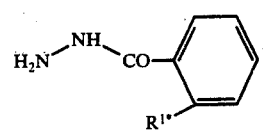

in which $R^{1*}$ repreents an alkyl group containing up to 6, or preferably up to 4, carbon atoms is reacted with 3-(5-nitro-2-furyl)acrylaldehyde.

In particular, the starting material comprises an aromatic carboxylic acid hydrazide of the formula

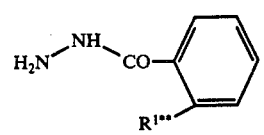

in which $R^{1**}$ represents a straight-chain alkyl group containing up to 4 carbon atoms.

Illustrative starting compounds comprise o-toluohydrazide (= o-tolylic acid hydrazide or o-methylbenzoic acid hydrazide) and o-ethylbenzhydrazide (= o-ethylbenzoic acid hydrazide).

The performance of the process is based on a mole ratio of 3-(5-nitro-2-furyl)acrylaldehyde to aroyl hydrazide of from about 0.8 to 1.3 : 1. A mole ratio of from 1 to 1.3 : 1 is preferred; an excess of aldehyde is advantageously employed. The reaction temperatures are between 0° and 100° C; the operation is carried out at temperatures up to the boiling point of the employed solvent. Temperatures of from 10° to 70° C are preferred. A solvent is generally used in which both the acrylaldehyde and the hydrazide are soluble but in which the final product formed is only sparingly soluble. Under the reaction conditions applied, the solvent should not react irreversibly with the hydrazide, with the aldehyde or with the resulting condensation-product. Preferred solvents are essentially inert with regard to reactants and reaction products. Exemplary solvents include low-molecular alkanols, for example methanol, ethanol, and isopropanol; low-molecular halogen hydrocarbons (halocarbons), for example dichloromethane and trichloroethylene; and aromatic hydrocarbons, provided that they have adequate dissolving power for the starting products.

More precisely, the procedure comprises adding a solution of aroyl hydrazide to a solution of 3-(5-nitro-2-furyl) acrylaldehyde while stirring, the stirring of the reaction mixture being continued until the hydrazone substance formed is precipitated because of its sparing solubility. The precipitate is separated and is advantageously recrystallized from a low-molecular alkanol, for example ethanol; from a low-molecular ketone, for example acetone; from an aromatic hydrocarbon, for example benzene; or from a mixture of such solvents.

The 3-(5-nitro-2-furyl)acrylaldehyde used as starting compound is known. It is obtained by aldol condensation of 5-nitrofurylaldehyde with acetaldehyde by the method of H. Saikachi et al. [*J. Amer. Chem. Soc.*, 80, 3642 (1958)]. A more favorable method of preparing the aldehyde, however, calls for reacting 5-nitrofurylaldehyde with methyl vinyl ether in the presence of boron trifluoride etherate. This method is preferred over aldol condensation with acetaldehyde because of better yield and greater purity of final product.

The compounds of the formulae II, II* and II**, which are used as starting materials, are known or are prepared from available starting materials by methods known per se.

For this purpose the corresponding aromatic o-alkylcarboxylic acids are first esterified, preferably under acid conditions, with alcohols, for example methanol or ethanol, and the resulting esters are then reacted with 100% hydrazine hydrate to form the corresponding hydrazines.

Alternatively, the corresponding o-alkylcarboxylic acid chlorides are reacted with hydrogen, the reaction advantageously taking place in the presence of an inert organic solvent and in the presence of a base. The preparation of o-tolylic acid hydrazide is, for example, described in *Beilstein*, 9, 467.

The new compounds of formulae I, I*, and I** are effective against bacteria (bacteriostatic agents and bactericides), and especially against protozoa (protozoacides), particularly against trichomonads. In addition, the compounds also possess activity against yeasts and fungi (fungistatic and fungicidal agents).

Infection tests with *Trichomonas foetus* confirm that the new nitrofuryl compounds possess excellent trichomonacida activity, this activity clearly exceeding that of metronidazole. The new compounds are thus trichomonacides.

The new nitrofuryl compounds are useful as chemotherapeutic agents for combatting trichomonads, their systemic action being regarded as of particular advantage.

Another aspect of the invention is therefore chemotherapeutically-active medicines for combatting provocative agents of human and animal disease processes. The new medicinal preparations are characterized by a content of one or more active substances of the formulae I, I* or I**.

In addition to the active substances, the new medicinesoptionally contain pharmaceutical vehicles for these active substances. The active substance content of these medicines constitutes from 1 to 95%, preferably from 10 to 85%, by weight of the prepared medicine.

In accordance with the invention the active substances is administered in any desired form provided that the formation or maintenance of an adequate blood or tissue level of nitrofuryl compound is assured. This is achieved by either parenteral or oral administration in suitable doses. The new medicines are alternatively administered rectally or topically (intravaginally). Pharmaceutical preparations of the active substance are advantageously presented in the form of unit doses adapted to a form desired for administration. A unit dose is, for example, a tablet, e.g. a vaginal tablet, a capsule, a suppository, a globula, or a suitable volumetric amount of a powder, of a granulate, of a solution, of an emulsion, of a suspension, of a gel or of an ointment.

The expression "unit dose" is herein understood to mean a physically-determined unit which contains an individual amount of the active constituent mixed with a pharmaceutical diluent for the same, or together with a pharmaceutical vehicle. The amount of active substance is selected so that a fixed number, e.g. one, of units are suitable for a single therapeutical administration.

The unit dose is, alternatively, divisible and, e.g., in the form of tablets provided with notches, if only a fraction, such as a half or a quarter, of the divisible unit is required for an individual therapeutic administration.

When prepared in unit dose form and intended for administration to mammals, for example to human beings, the pharmaceutical preparations of the invention contain from 50 to 500 milligrams, preferably about 150 to 300 milligrams, and in particular about 175 to 250 milligrams of active substances. For larger mammals the individual dose varies from 500 to 5000 milligrams, preferably from about 750 to 2000, milligrams of active substance. When administered to birds, for example doves or hens, it varies from 0.1 to 50, preferably from about 0.5 to 20, milligrams (mg). Therapeutic administration of the pharmaceutical preparation is effected from once to four times a day at fixed or varying times, for example after each meal and/or in the evening. The dose administered depends on the frequency of the administration, the duration of the treatment, the nature and seriousness of the illness, and the weight, age and the state of health of the patient.

The daily dose for mammals is generally between 0.05 and 70.0 mg per kilogram (kg) of body weight and, for human beings, preferably between 3 and 50 mg per kg of body weight.

The pharmaceutical preparations usually consist of active substances (compound of formula I) and of non-toxic pharmaceutically-compatible medicament vehicle, used as an additive in solid, semi-solid, or liquid form or as a coating medium, for example in the form of a capsule, tablet coating, bag, or other container for the therapeutically active constituent. Vehicles serve, for example, to assist absorption of the medicine by the body, as a formulation adjuvant, as a sweetening agent, as a taste corrector, as a coloring agent, or as a preservative.

For oral application use is made of tablets, sugar-coated pills, hard or soft, for example gelatine capsules, dispersible powders, granulates, aqueous and oily suspensions, emulsions, solutions, or syrups.

Tablets optionally contain inert diluents, for example calcium carbonate, calcium phosphate, sodium phosphate, or lactose; granulating and distribution media, for example maize starch or alginates; binders, for example starch, gelatine, or acacia gum; and lubricants, for example aluminum or magnesium stearate, talcum, or silicone oil.

Tablets are optionally additionally provided with a coating which assures delayed dissolution and resorption of the medicine in the gastrointestinal tract and thus ensures, for example, better tolerability, protraction, or retardation. Gelatine capsules contain the medicine e.g., mixed with a solid diluent, for example calcium carbonate or kaolin, or with an oily diluent, for example olive oil, groundnut oil, or paraffin oil.

Aqueous suspensions contain, e.g., suspension agents, for example sodium carboxymethyl cellulose, methyl cellulose, hydroxypropyl cellulose, sodium alginate, polyvinyl pyrrolidone, gum tragacanth, or acacia gum; dispersion and wetting agents, for example polyoxyethylene stearate, heptadecaethyleneoxycetanol, polyoxyethylene-sorbitol monooleate, polyoxyethylenesorbitan monooleate, or lecithin; preservatives, for example methyl or propyl hydroxybenzoate; taste imparting agents; sweetening agents, for example saccharose, lactose, sodium cyclamate, dextrose or invert sugar syrup.

Oily suspensions, for example, contain ground nut oil, olive oil, sesame oil, coconut oil, or paraffin oil, and thickening agents, such as beeswax, hard paraffin, or cetyl alcohol; also sweetening agents, taste imparting agents, and antioxidants.

Powders and granulates which are dispersible in water optionally contain the medicines mixed with dispersion, wetting, and suspension agents, for example those mentioned above, and also with sweetening agents, taste imparting agents, and coloring agents.

Emulsions, for example, contain olive oil, groundnut oil, or paraffin oil, together with emulsifying agent, such as acacia gum, gum tragacanth, phosphatides, sorbitan monooleate, polyoxyethylenesorbitan monooleate, and sweetening and taste imparting agents.

For rectal administration of the medicines use is made of suppositories, which are prepared with the aid of binders melting at rectal temperature, for example cocoa butter or polyethylene glycols.

For parenteral application of the medicines use is made of sterile injectable aqueous suspensions, isotonic salt solutions, or other solutions, which contain, e.g., dispersion or wetting agents and/or pharmacologically-compatible diluents, for example propylene glycol or butylene glycol.

In addition to the new 5-nitrofuryl compounds the pharmaceutical preparations, for example, contain one or more compatible pharmacologically active constituents from other medicament groups, for example steroids, such as estrogens, for example estradiol benzoate or estradiol valerianate, or corticoids, for example hydrocortisone; sulphonic acid amides, for example sulphanilamide or 6-sulphanilamido-2,4-dimethyl pyrimidine; antibiotics, such as penicillins, for example penicillin G or ampicillin, cephalosporins, for example cephalosporin C, or saccharide antibiotics, such as streptomycins, kanamycins or neomycins, or polyene antibiotics, for example nystatin, pimaricin, or amphotericin B, or tetracyclins, for example Aureomycin® or Terramycin®, or peptide antibiotics, for example polymyxin, bacitracin; nitroheterocyclics, such as nitrothiazoles, for example 2-(2-thenoylamino)-5-nitrothiazole or nitrofurantoin, or nitropyrimidins, such as 2-amino-5-nitropyrimidine; antimycotics, such as phenolcarboxylic acids, for example o-hydroxybenzoic acid or p-hydroxybenzoic acid alkyl ester, or 8-hydroxyquinolines, for example 5-chloro-8-hydroxy-7-iodoquinoline or 5,7-dichloro-8-hydroxyquinaldine.

Another aspect of the invention is chemotherapy for animals, for example mammals or birds, suffering from trichomoniasis.

Accordingly, a therapeutically-effective and pharmacologically-tolerable amount of one or more compounds of formula I, I*, or I** is administered to a sick animal, for example a mammal or bird. This treatment is particularly suitable for diseases caused by *Trichomonas vaginalis, Trichomonas foetus*, or *Trichomonas gallinae*.

The following examples explain the invention in greater detail, without restricting it. Temperatures are in ° C, and all parts are by weight unless otherwise specified. The relationship between parts by weight (w) and parts by volume (v) is the same as that between a kilogram and a liter (l).

EXAMPLE 1

5-nitro-2-[(o-toluoylhydrazono)propen-1-yl]furan 1. o-toluoyl hydrazide 54.4 parts of o-toluoylic acid are heated for 8 hours under reflux with 200 parts of methanol in the presence of 25 parts of concentrated sulfuric acid. After methanol is distilled off, the reaction product is dissolved in chloroform and the resulting solution is extracted with a sodium carbonate solution in order to dissolve unesterified o-toluoylic acid. The chloroform phase is mixed with 100% hydrazine hydrate in the molar ratio, 1:1.2, and is heated to distil off the chloroform. After cooling, the hydrazide is obtained in crystalline form and is recrystallized from methanol. M.P. 125° C.

2. 3-(5-nitro-2-furyl)acrylaldehyde 25 parts of 5-nitro-2-furylaldehyde are dissolved in 60 parts of benzene and mixed at from 0° to 5° C with 14.5 parts of acetaldehyde. A solution of 0.32 part of piperidine and 0.5 part of glacial acetic acid in 25 parts of benzene is added thereto a drop at a time and the resulting admixture is kept at from 5° to 10° C for 10 hours. The temperature of the reaction solution is then allowed to rise slowly to room temperature (20° C), at which it is kept for 6 hours before being heated for 6 more hours at 60° C. After cooling, a red resin-like reaction product is obtained. From this reaction product 13 parts (44 percent of the theoretical) of 3-(5-nitro-2-furyl) acrylaldehyde (having a melting point of 118° C) are obtained by extraction with hot methylene chloride or with benzene.

3. 5-nitro-2-[(o-toluoylhydrazono)propen-1-yl]) furan 15 parts of o-toluoyl hydrazide (dissolved in 200 parts of ethanol) are added, while stirring, to a solution of 18.4 parts of 3-(5-nitro-2-furyl)acrylaldehyde in ethanol. After a short time, a yellow precipitate forms: This precipitate is sucked off and recrystallized from ethanol/acetone. 22 parts of 5-nitro-2-[(o-toluoylhydrazono)propen-1-yl]furan [melting point: 208° C (with decomposition)] are thus obtained. Yield: 73.5% of the theoretical.

EXAMPLE 2

2-[(o-ethylbenzoylhydrazono)propen-1-yl]-5-nitrofuran

Following the procedure of Example 1, o-ethylbenzhydrazide is obtained from o-ethylbenzoic acid and is further reacted without final recrystallization. 10.2 parts of o-ethylbenzoylhydrazine are mixed with 200 parts of an approximately 13% (w/v) solution of 3-(5-nitro-2-furyl)acrylaldehyde in dichloromethane, and the resulting admixture is stirred at room temperature. After some hours, a crystalline precipitate starts to form. The mixture is stirred for one more hour, the solvent is drawn off, and impurities are removed by stirring with benzene. The residue is washed with benzene in a suction filter and dried. 14.5 parts of a yellow substance [melting point: 186° to 188° C (76% of the theoretical)] are obtained in pure form (thin layer chromatography).

EXAMPLE 3

5-nitro-2-[(o-butylbenzoylhydrazono)propen-1-yl]furan 1. ethyl o-bromomethylbenzoate 35 grams (g) of o-bromomethylbenzoic acid are heated in 250 ml of thionyl chloride, in the presence of a few drops of dimethylformamide, until no further gas is produced. Excess thionyl chloride is thereupon distilled off, and cooled liquid residue is heated for 3 hours under reflux with the calculated amount of absolute ethanol. Purification is effected by column chromatography. Yield: 30 g (75% of the theoretical).

IR: $\nu$ CO1740 cm$^{-1}$

NMR: [solvent (CH$_3$)$_2$SO, internal standard tetramethylsilane]: $\delta$ = 1.35 ppm(t), CH$_3$; $\delta$ = 4.3 ppm (q), OCH$_2$; $\delta$ = 5.05 ppm (s), CH$_2$Br; 7.3–8.0 ppm(m), aromatic protons.

2. (o-ethoxycarbonylbenzyl)triphenylphosphonium bromide 20 g of the ester described under (1) above are mixed with a solution of 28 g of triphenyl phosphine in 250 ml of benzene, and the mixture is heated to boiling for about 290 hours. The precipitated phosphonium salt is sucked off and dried.

M.P. 195° to 198°.

Yield: 38 g (91% of the theoretical).

3. ethyl o-(1-butenyl)benzoate

A suspension of 38 g of the phosphonium bromide described under (2) above in 500 ml of absolute (abs.) tetrahydrofuran are mixed (a drop at a time), in a protective gas atmosphere, with 40 ml of a 2.5 molar solution of butyl lithium in n-heptane. 6 milliliters (ml) of propionaldehyde (dissolved in 20 ml of abs. tetrahydrofuran) are added slowly to the resulting orange-red solution, and the resulting admixture is heated under reflux for 20 hours. After the formed triphenylphosphine oxide is filtered off and the filtrate is concentrated by evaporation, and the liquid residue is purified by column chromatography.

Yield: 7.7 g (50% of the theoretical)

IR spectrum: $\nu$ CO 1720 cm$^{-1}$

NMR: (solvent CCl$_4$, internal standard tetramethylsilane):

$\delta$ =

0.9 – 1.5 (m), 2 CH$_3$ groups 1.7 – 2.4 (m) CH$_2$—CH=

4.0 – 4.5 (q) OCH$_2$ 5.4 – 6.3 (m) CH$_2$—CH=

6.9 – 7.5 (m) aromatic protons 7.7 – 8.0 (m) =CH—Ar 4. o-(n-butyl)benzhydrazide

A solution of 7.5 g of the ester described above under (3) in 100 ml of ethanol is treated with hydrogen in the presence of a Pd/C catalyst. After absorption of the theoretical amount of hydrogen, the solution is filtered off from the catalyst, the filtrate is concentrated by evaporation, and the uniform (thin layer chromatography) residue is heated for about 25 hours under reflux together with 50 ml of hydrazine hydrate. Distribution between water and chloroform, drying of the organic phase, and evaporation lead to a semi-solid product which is purified by column chromatography.

M.P. 78° to 80°.

Yield: 1.7 g (26% of the theoretical).

5. 5-nitro-2-[(o-butylbenzoylhydrazono)propen-1-yl]furan

A solution of 1.7 g of the butyl benzhydrazide mentioned under (4) above in 20 ml of dichloromethane is mixed with a solution of 3.5 g of 3-(5-nitro-2-furyl)acrylaldehyde in 20 ml of dichloromethane, and the mixture is stirred at room temperature. The yellow-brown product (precipitated after a reaction time of 3 hours) is sucked off, the filtrate is concentrated, and the resulting solid material is likewise isolated. The two precipitates are recrystallized together from 200 ml of ethanol.

M.P. 212° to 213°.

Yield: 1.5 g (50% of the theoretical).

EXAMPLE 4

5-nitro-2-[(o-toluoylhydrazono)propen-1-yl]furan tablets containing 175 mg of active substance Production of a batch of 100,000 tablets.

| | |
|---|---|
| 1. 5-nitro-2-[(o-toluoylhydrazono)propen-1-yl]-furan (micronized) | 17.500 kg |
| 2. Lactose | 7.500 kg |
| 3. Potato starch | 6.000 kg |
| 4. Polyvinylpyrrolidone (having a mean molecular weight of 25,000) | 1.000 kg |
| 5. Carboxymethyl cellulose | 2.650 kg |
| 6. Magnesium stearate | 0.350 kg |
| | 35.000 kg |

Ingredient 1 is ground in an air jet mill to a particle size of 10 microns ($\mu$) and homogeneously mixed with the indicated amounts of ingredients 2 and 3. This mixture is well wetted with a solution of ingredient 4 in sever liters of water and is granulated through a sieve of a mesh of 1.5 mm. The granulate is dried in a fluidized bed dryer to a relative moisture content of 50 to 60% and is homogeneously mixed with the indicated amounts of ingredients 5 and 6. After sifting, the granulate is pressed into tablets of 350 mg, with a diameter of 10 millimeters (mm) and with a breaking notch.

The tablets are administered to female patients suffering from trichomoniasis. One tablet is administered orally 2 to 3 times a day; after treatment for one week, it is no longer possible to detect any living trichonomonads in the vaginal secrection of the women.

EXAMPLE 5

2-[(o-ethylbenzoylhydrazono)propen-1-yl]-5-nitrofuran tablets containing 200 mg of active substance.

Production of a batch of 100,000 tablets.

| | |
|---|---|
| 1. 2-[(o-ethylbenzoylhydrazono)propen-1-yl]-5-nitrofuran (micronized) | 20.000 kg |

-continued

| | |
|---|---|
| 2. Lactose | 9.500 kg |
| 3. Potato starch | 6.000 kg |
| 4. Polyvinylpyrrolidone (having a mean molecular weight of 90,000) | 1.000 kg |
| 5. Carboxymethyl cellulose | 3.100 kg |
| 6. Magnesium stearate | 0.400 kg |
| | 40.000 kg |

Ingredient 1 is ground in an air jet mill to a particle size below 10 μ and is homogeneously mixed with the indicated amount of ingredients 2 and 3. This mixture is well wetted with a solution of ingredient 4 in 7.5 liters of water and is granulated through a sieve of a mesh of 1.5 mm. The granulate is dried in a fluidized bed dryer to a relative moisture content of from 50 to 60% and is homogeneously mixed with the indicated amount of ingredients 5 and 6. After sifting, the granulate is pressed into tablets (provided with a breaking notch) of 400 mg and 11 mm in diameter.

These tablets, like those of Example 1, are similarly suitable for treating patients suffering from trichmoniasis.

EXAMPLE 6

5-nitro-2-[(o-toluoylhydrazono)propen-1-yl]furan injection solution for veterinary use.

10 ml contains 875 milligrams (mg) of active substance.

Preparation of a batch of 100 liters.

| | |
|---|---|
| 1. 5-nitro-2-[(o-toluoylhydrazono)propen-1-yl]furan | 8.750 kg |
| 2. N,N-dimethylacetamide | 42.000 kg |
| 3. Glycerinformal | 18.000 kg |
| 4. 1,3-butylene glycol | 16.000 kg |
| 5. Physiological sodium chloride solution to make 100 liters | |

Ingredient 1 is dissolved in a mixture of ingredients 2, 3, and 4 at 50° and made up to 100 liters with ingredient 5. The solution is filtered through a Seitz filter (EKS) and filled into 10 ml ampoules. The filled ampoules are sterilized for 1 hour at 100° C.

EXAMPLE 7

2-[(o-ethylbenzoylhydrazono)propen-1-yl]-5-nitrofuran injection solution for a veterinary use.

10 ml contain 1000 mg of active substance.
Production of a batch of 100 liters.

| | |
|---|---|
| 1. 2-[(o-ethylbenzoylhydrazono)propen-1-yl]-5-nitrofuran | 10.000 kg |
| 2. N,N-dimethylacetamide | 40.000 kg |
| 3. Glycerinformal | 19.000 kg |
| 4. 1,3-butylene glycol | 16.000 kg |
| 5. Physiological sodium chloride solution to make 100 liters. | |

Ingredient 1 is dissolved in a mixture of ingredients 2, 3, and 4. It is then made up to 100 liters with ingredient 5. The solution is then subjected to sterile filtration in a Seitz filter (EKS) and is filled into 10 ml ampoules. The filled ampoules are sterilized for 1 hour at 100° C.

EXAMPLE 8

Vaginal tablets with 500 mg active substance:

| | |
|---|---|
| 1. 5-nitro-2-[(o-toluoylhydrazono)propen-1-yl]furan | 50 kg |
| 2. Lactose | 50 kg |
| 3. Carboxymethyl cellulose | 16 kg |
| 4. Talc | 4 kg |
| | 120 kg |

1, 2, and 3 are mixed, wetted with 3 l of water and granulated through a sieve with a mesh of 1.5 mm. The granulate is dried in a fluidised bed dryer to a relative humidity of 50 to 60%, mixed with 4 and, after sieving, is compressed into tablets of 1200 mg.

In special cases it may be indicated to administer one of these vaginal tablets to the sick woman every evening for several days, in addition to the administration of tablets.

The effectiveness of the compounds of Examples 1 and 2 against trichomonades in comparison with metronidazol was determined by the following test procedure. Based on the method described by E. Kutter, H. Machleidt, W. Reuter, R. Sauter, and A. Wildfeuer in Arzneimittelforschung, 22, 1045 et seq. (1972), 500,000 Trichomonas foetus trichomonades (adjusted under the phased contrast microscope in a Neubauer counting chamber) in 0.5 ml of a 24-hour old culture [in fluid thioglycolate medium with 10% bovine serum and with the addition of neomycine sulfate corresponding to 33 micrograms (μ g) of neomycine base and 2.5 units of bacitracin/ml] were injected i.p. into male NMRI mice of a weight of from 20 to 22 g. The substances were respectively suspended in a 1% aqueous suspensions of carboxymethyl cellulose (Tylose® C 1000 p) by homogenization with a stirrer. 0.2 ml of the suspensions was administered to the mice by means of a stomach tube, so that the doses indicated in Table 1 below were obtained.

In order to maintain the stock, about 1 ml of exudate containing Trichomonas foetus was taken 3 to 4 days after the infection, under sterile conditions, and inoculated with the previously mentioned nutrient solution in amounts of about 0.1 ml in tubes. If the culture has grown well after 24 hours, a new test batch can be made for testing substances. In order to keep the Trichomonas foetus alive and capable of infection during periods between tests, from 0.2 to 0.5 ml of freshly taken exudate is transferred to mice at the respective interval of from 3 to 4 days.

The results can be seen from Table 1.

TABLE 1

Infection tests with Trichomonas foetus
(500,000 trichomonades in 0.5 ml i.p., NMRI mice, 21 to 22 g, treatment on 3 successive days on the first occasion 1 hour after treatment)

| Compound | Dose mg/kg | Number of Animals Tested | % of Animals Dying After Infection (Mean Value) |
|---|---|---|---|
| 5-nitro-2-[(o-toluoyl-hydrazono)propen-1-yl]furan (A) | 12.5 | 60 | 3.33 |
| | 6.25 | 60 | 36.33 |
| | 3.12 | 60 | 91.66 |
| 2-[(o-ethylbenzoyl-hydrazono)propen-1-yl]5-nitrofuran (B) | 25 | 10 | 0 |
| | 12 | 50 | 6 |
| | 6.25 | 50 | 46 |
| | 3.12 | 50 | 62 |
| | 1.56 | 50 | 86 |
| Metronidazol | 100 | 50 | 4 |
| | 75 | 10 | 0 |
| | 50 | 40 | 15 |
| | 25 | 70 | 70 |
| | 12.5 | 50 | 80 |
| | 6.25 | 90 | 90 |

The LD$_{50}$ values (in the mouse) of compounds A and B and of metronidazol are above 2 g/kg.

The activity of the compounds of the invention is further confirmed from the activity of the compound of Example 1 (A) with regard to Klebs. pneum. PCI 602, E. coli 6106, Ps. aeruginosa 2, Staph. aur. SG 511, Staph. aur. PCI 1203, streptococci group A 807, streptoc. group B 779, streptococci group C 805, enterococci, C. Albicans 49, C. Paracrusei 45 in comparison with metronidazol.

For the purpose of carrying out in vitro growth inhibiting tests, suspensions (made with 0.85% sterile NaCl solution) of 18-hour-old agar slant or Sabouraud agar slant cultures or, in the case of streptococci or enterococci, cultures of corresponding age in a glucose bouillon are adjusted to an extinction of 0.200 in a photometer (ELKO II) against $H_2O$, and (as blank value) uninoculated glucose bouillon, in a 0.5 centimeter (cm) vessel, utilizing filter S 75. For the test, glucose bouillon [or in the case of yeast, Sabouraud bouillon with dextrose 1:100] is inoculated with the adjusted germ suspension. In order to facilitate the reading, the glucose bouillon contains 0.1% of a 2% aqueous water blue solution.

Stock solutions containing 5,000 $\mu$g/ml are made of the test substances and are diluted at a rate of 1 : 10 with the inoculated nutrient solution, so that the concentration in the first tubes of the dilution series correspond in each case to 500 $\mu$g/ml. By means of pipette transfer, dilution series with concentration falling by half each time, that is to say 500, 250, 125 $\mu$g/ml, etc., are prepared. The volume of the dilution series in the individual tube amounts in each case to 2 ml. After incubation for 24 and 48 hours at 37°, the individual tubes are spread out on nutrient agar containing no active substance, or on Sabouraud agar in the case of yeasts. These subcultures are also read after incubation for 24 and 48 hours at 37°. The columns showing the dilution series in Table 2 indicate the minimum inhibition concentrations after incubation for 24 and 48 hours, while the subculture columns show the concentrations from which the subcultures no longer started.

($Na_2HPO_4 \cdot 2H_2O$ = 7g; $KH_2PO_4$ = 3 g; NaCl = 4 g; dist. $H_2O$ = 1000 ml) and made up to 10 ml.

The Serratia marcescens strain HY/a 21, starting from the above suspension, is diluted in a buffered NaCl solution. 0.2 ml of the dilution is spread out on serratia minimal agar. After incubation for 60 minutes at 30°, sterile filter paper sheets of a diameter of 2 cm are applied and 0.05 ml of the test solution is pipetted on to them by means off a microtitration pipette. The plates are incubated for 3 to 4 days at 30°. The prototrophic colonies are then counted.

After the incubation period the colonies occurring in concentrated form around an inhibition center without growth are counted (without taking into account the auxotrophic background growth). For control purposes a plate with a filter paper test sheet without active substance is also applied.

| Minimal nutrient medium for Serratia marcescens HY/a 21 | | |
|---|---|---|
| Stock solution | | |
| $(NH_4)H_2PO_4$ | | 30 g |
| Citric acid | | 50 g |
| (or sodium citrate $2H_2O$ = 54.5 g) | | |
| NaCl | | 3 g |
| $MgSO_4 \cdot 7H_2O$ | | 3 g |
| $CaCl_2$ | | 0.5 g |
| (or saturated solution - 0.3 ml) | | |
| KOH | | 62 g |
| Glycerine | | 238 ml |
| Trace solution (T) | | 10 ml |
| (added in sterile filtered form after sterilization) | | |
| $H_2O$ (600 ml) | to make | 1000 ml |

Sterilize for 15 minutes at 1 atmosphere gauge. Adjust pH to 7.0 with NaOH (after sterilization).

| Solution T | | |
|---|---|---|
| $T_1$ : $CaCl_2$ | | 1.0 g / 10 ml $H_2O$ |
| $T_2$ : $MgSO_4 \cdot 7H_2O$ | | 10 mg |
| $FeSO_4 \cdot 7H_2O$ | | 25 mg |
| Thiamin dihydrochloride | | 10 mg |
| Distilled water | to make | 90 ml |

Table 2

Test of the antibacterial action of A in comparison with metronidazol
Minimum inhibiting concentration (MHK) in $\mu$g/ml

| | Series dilution test, read after | | | | Subcultures applied after | | | | | | | |
|---|---|---|---|---|---|---|---|---|---|---|---|---|
| | | | | | 24 h read after | | | | 48 h read after | | | |
| | 24 h | | 48 h | | 24 h | | 48 h | | 24 h | | 48 h | |
| Strain | A | Metronidazol | A | Metronidazol | A | Metronidazol | A | Metronidazol | A | Metronidazol | A | Metronidazol |
| Klbs. pneum. PCI 602 | 7.8 | >500 | 7.8 | >500 | 31.25 | >500 | 31.25 | >500 | 31.25 | >500 | 31.25 | >500 |
| E. coli 6106 | 31.25 | >500 | 62.5 | >500 | 62.5 | >500 | 62.5 | >500 | 62.5 | >500 | 62.5 | >500 |
| ps. acrug. 2 | 250 | >500 | 250 | >500 | 250 | >500 | 250 | >500 | 250 | >500 | 250 | >500 |
| Staph. aur. SG 511 | 31.25 | >500 | 31.25 | >500 | 125 | >500 | 125 | >500 | 31.25 | >500 | 31.25 | >500 |
| Staph. aur. PCI 1203 | 15.6 | >500 | 31.25 | >500 | 31.25 | >500 | 31.25 | >500 | 31.25 | >500 | 31.25 | >500 |
| Strepto. Gr.A 807 | 31.25 | >500 | 31.25 | >500 | 125 | >500 | 125 | >500 | 62.5 | >500 | 125 | >500 |
| Strepto. Gr. B 779 | 250 | >500 | 500 | >500 | 500 | >500 | 500 | >500 | 500 | >500 | 500 | >500 |
| Strepto. Gr. C 805 | 250 | >500 | 250 | >500 | 500 | >500 | 500 | >500 | 500 | >500 | 500 | >500 |
| Enteropkokken | 62.5 | >500 | 250 | >500 | 250 | >500 | 250 | >500 | 500 | >500 | 500 | >500 |
| C. sibicann 49 | 62.5 | >500 | 62.5 | >500 | 62.5 | >500 | 62.5 | >500 | 125 | >500 | 125 | >500 |
| C. paracruaci 45 | 62.5 | >500 | 125 | >500 | 125 | >500 | 125 | >500 | 125 | >500 | 125 | >500 |

In vitro tests for testing a questionable mutagenic action were carried out on the basis of the test arrangement of G. Mohn (Arch. Toxikol. 28, 93, 1971) and of G. Mohn and R. W. Kaplan (Mol. Gen. Genetics., 99, 191, 1967).

In vitro mutation tests on a fixed nutrient medium 10 ml of 18 hour old nutrient broth cultures of the auxotrophic Serratia marcescens strain HY/a 21 are twice washed with sterile buffered NaCl solution Mix $T_1$ and $T_2$ and filter under sterile conditions.
1.8 to 2% Difco Bacto Agar solution 900 ml
Stock solution 100 ml Mixing is effected under sterile conditions and the mixture is immediately poured onto plates.

Aqueous solutions of (in each case) 10 mg/ml are made of the control substances, N-methyl-N'-nitro-N-nitrosoguanidine and $\beta$-propiolactone. 0.05 ml of each of these solutions is applied by dropping to the previously-described test sheets used.

10 mg of 5-nitro-2-[(o-toluoylhydrazono)-1yl]furan (A) are dissolved in each case in 1 ml of dimethyl formamide 10 mg of metronidazol are dissolved in 1 ml of distilled water with slight heating. 0.05 ml of the solutions is applied by dropping onto the filter paper sheets. The results are shown in Table 3a.

TABLE 3a

In vitro mutagenicity tests on a solid nutrient medium (spot test) with the auxotrophic serratia marcescens strain HY/21.

|  |  | Strain colonies/ml HY/a21 | | |
|---|---|---|---|---|
| Substance | mg/ml | Number of germs | Mutants Spontaneous Test | Mutation frequency |
| Metronidazol | 10 mg | $1.9 \times 10^8$ | $3.5 \times 10^2$   $5.9 \times 10^2$ | $3.1 \times 10^{-6}$ |
| N-methyl-N'-nitro-N-nitro soguanidine | 10 mg | $1.9 \times 10^8$ | $3.5 \times 10^2$   $6.45 \times 10^2$ | $3.3 \times 10^{-6}$ |
| β-propio-lactone | 10 mg | $1.9 \times 10^8$ | $3.5 \times 10^2$   $6.6 \times 10^2$ | $3.4 \times 10^{-6}$ |
| A | 10 | $1.8 \times 10^8$ | $2.5 \times 10^1$   $1.5 \times 10^1$ | 0 |
| A | 5 | $1.8 \times 10^8$ | $2.5 \times 10^1$   $1.0 \times 10^1$ | 0 |

Host Mediated Assay

A Host Mediated Assay is carried out on the basis of the test arrangement of M. S. Legator, described in "Chemical Mutagenesis in Mammals and Man," edited by F. Vogel and G. Röhrborn, Springer Verlag 1970, and of P. Propping and W. Buselmaier, *Arch. Toxikol.*, 28, 129–134, 1971.

Starting with a stock culture of *S. typhimurium* G 46 of tryptone agar, a 20 hour old culture of this strain, incubated at 37°, is applied in tryptone water. 50 ml of tryptone water are addded to 4 ml of this 20-hour-old culture and the mixture is incubated for 1 hour at 37°. 12 NMRI mice of a body weight of from 25 to 36 g are injected i.p. with 2 ml of this culture in each case. 6 mice serve as test animals and 6 as control animals. At the same time the substances being tested are administered s.c. or per os in 0.1 to 0.5 ml of aqueous solution. 3 hours after infection 2 ml of 0.85% sterile NaCl solution are injected i.p. and the mice are then killed. The abdominal skin is opened in V-shape under sterile conditions. As much liquid as possible (1.5–2.0 ml) is taken out under sterile conditions with a sterile syringe. With the exudate obtained, dilutions with sterile 0.85% NaCl solution are applied. For the purpose of checking the number of germs, 0.05 ml of the dilutions $10^{-5}$ to $10^{-7}$ are applied by dropping on to the surface of endo agar, the drop being slightly widened out with the tip of the pipette. One endoplate is used per dilution. After incubation overnight at 37°, the total number of germs is determined.

For the purpose of determining the mutation rate, 0.05 ml of each of the undiluted suspension and of the 1 : 10 diluted suspension are similarly applied by dropping on to a plate with Spizizen's minimal agar. After incubation for 48 hours at 37°, the minimal agar plates are counted. The number of germs counted is related to the total number of germs.

Special nutrient media used:

| 1. Tryptone agar | |
|---|---|
| Bacto tryptone | 5 g |
| Bacto agar | 20 g |
| Dist. water | 1000 ml |

Autoclave for 15 minutes at 1.2 atmospheres gauge.

| 2. Tryptone water | |
|---|---|
| Bacto tryptone | 5 g |
| Dist. water | 1000 ml |

| 3. Spizizen's minimal nutrient medium | |
|---|---|
| 5 % sterile filtered glucose solution | 100 ml |
| 2 % bacto agar solution | 650 ml |
| 4-salt solution | 250 ml |

Autoclave for 15 minutes 1.2 atmospheres gauge.

| 4-salt solution | | |
|---|---|---|
| $(NH_4)_2SO_4$ | | 8 g |
| $K_2HPO_4 3H_2O$ | | 56.0 g |
| $KH_2PO_4$ | | 24.0 g |
| Trisodium citrate | | 4.0 g |
| $MgSO_3$ | | 0.8 g |
| Dist. water | to make | 1000 ml |

| 4. Endo agar | | |
|---|---|---|
| Peptone from meat, tryptically digested, Merck Lab-Lemco meat extract, neutral, powdered, (Oxoid) | | 10 g |
| | | 10 g |
| NaCl | | 5 g |
| Powdered agar | | 20 g |
| Dist. Water | to make | 1000 ml |

Autoclave for 30 minutes at 120° C.
pH after sterilization 7.4–7.5.

One liter of this prepared nutrient agar is liquefied in hot water.

| Nutrient agar | 1000 ml |
|---|---|
| 50 % sterile filtered lactose solution | 20 ml |
| Saturated alcoholic fuchsin solution | 4 ml |

After mixing the hot nutrient medium, sufficient freshly prepared 10% hot sodium sulphite solution (about 15 ml) is added to give the hot nutrient medium a just-pink colored appearance.

The results are indicated in Table 3b.

Table 3b

| Substance | Dose/animal and application | Host mediated assay with Number of control germs ml Test animals | Host mediated assay with Number of control germs ml Control animals | Mutants ml Test | Mutants ml Control | Spontaneous mutation frequency in control animals | Mutation frequency in test animals |
|---|---|---|---|---|---|---|---|
| A | 400 mg/kg per os | $6.44 \cdot 10^8$ | $8.9 \cdot 10^8$ | 0 | 0 | 0 | 0 |
| A | 200 mg/kg per os | $7.4 \cdot 10^8$ | $8.9 \cdot 10^8$ | 0 | 0 | 0 | 0 |
| Metronidazol | 200 mg/kg per os | $1.08 \cdot 10^8$ | $1.26 \cdot 10^9$ | $5.01 \cdot 10^1$ | 0 | 0 | $4.6 \cdot 10^{-7}$ |
| N-methyl-N'-nitro-N-nitroso-guanidine | 50 mg/kg s.c. | $1.02 \cdot 10^9$ | $8.9 \cdot 10^8$ | $5.94 \cdot 10^2$ | 0 | 0 | $5.82 \cdot 10^{-7}$ |

5-nitro-2-[(o-toluoylhydrazono)propen-1-yl]furan (A) and 2-[(o-ethylbenzoylhydrazone)propen-1-yl]-5-nitrofuran (B) have substantially better activity in mice infected with *T. foetus* 1 than metronidazol. Thus, when treated with a dose of 6.25 mg/kg of A and of B, 63.3% and 54%, respectively, of the animals survived, whereas the survival rate with metronidazol was only 10% (Table 1).

In the in vitro tests with 9 bacteria and 2 yeast strains metronidazol is ineffective even with the high concentration of 500 μg/ml, whereas A gives a substantially more favorable picture (Table 2).

In the in vitro mutagenicity tests (Table 3a) and also in the i.p. host mediated assay with *S. thyphimurium* (Table 3b), no mutants induced by A are observed. On the other hand, for the *Serratia marcescens* strain HYa21, metronidazol produced an approximately equally high mutation rate to that with N-methyl-N'-nitro-N-nitrosoguanidine or β-propiolactone. In the host mediated assay, moreover, metronidazol showed a certain mutagenic action even at 200 mg/kg, which demonstrates the superiority of compounds according to the invention.

What is claimed is:

1. A microbicidal 2-{[o-(lower)alkylaroylhydrazone]-propen-1-yl}-5-nitrofuran which is essentially non-toxic to mammals and birds upon administration thereto in microbicidally-effective doses and the aroyl of which comprises one ring, which is a 6-membered carbocyclic ring, or a mixture of such microbicidal nitrofurans.

2. A compound according to claim 1 in which the aroyl is benzoyl or benzoyl having one further ring substituent selected from the group consisting of chloro, bromo, hydroxyl, nitro, amino and alkyl having from 1 to 4 carbon atoms.

3. A nitrofuryl compound according to claim 1 wherein the o-alkyl has from 1 to 6 carbon atoms and the aroyl has only one or no further ring substituents, such further ring substituent, when present, being chloro, bromo, hydroxyl, nitro, amino or alkyl having from 1 to 4 carbon atoms.

4. A nitrofuryl compound according to claim 3 wherein the aroyl has no further ring substituents.

5. A nitrofuryl compound according to claim 4 wherein the o-alkyl has from 1 to 4 carbon atoms.

6. A nitrofuryl compound according to claim 5 wherein the o-alkyl is straight-chain alkyl.

7. The nitrofuryl compound according to claim 6 which is 5-nitro-2-[(o-toluoylhydrazono)propen-1-yl]furan.

8. The nitrofuryl compound according to claim 6 which is 2-[(o-ethylbenzoylhydrazono)propen-1-yl]-5-nitrofuran.

9. A process for chemotherapeutically treating an animal afflicted with trichomoniasis which comprises administering to the animal a therapeutically-active and pharmacologically-tolerable amount of at least one compound according to claim 1.

10. A process according to claim 9 wherein the animal is a mammal.

11. A process according to claim 10 wherein the mammal is a human.

12. A process according to claim 9 wherein the animal is a bird.

13. A therapeutically-active and pharmaceutically-acceptable medicament comprising a pharmaceutical vehicle and havingg a microbicidally-effective concentration of nitrofuryl microbicide according to claim 1.

14. A therapeutically-active and pharmaceutically-acceptable medicament in capsule form and containing a sufficient amount of nitrofuryl microbicide according to claim 1 to form or maintain a microbicidal blood or tissue level upon oral administration.

15. A therapeutically-active and pharmaceutically-acceptable medicament in a coated dosage form and containing a microbicidally-effective concentration of nitrofuryl microbicide according to claim 1.

16. A medicament according to claim 13 having from 1 to 95 percent by weight of the nitrofuryl microbicide.

17. A medicament according to claim 13 having from 10 to 85 percent by weight of the nitrofuryl microbicide.

18. A medicament according to claim 17 wherein the nitrofuryl microbicide is a mixture of such compounds.

* * * * *